United States Patent
Habben et al.

(10) Patent No.: US 7,265,219 B2
(45) Date of Patent: Sep. 4, 2007

(54) AUXIN-REPRESSED, DORMANCY-ASSOCIATED PROMOTER AND USES THEREOF

(75) Inventors: Jeffrey E. Habben, Urbandale, IA (US); Shuping Jiao, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 391 days.

(21) Appl. No.: 10/702,812

(22) Filed: Nov. 6, 2003

(65) Prior Publication Data

US 2004/0139506 A1 Jul. 15, 2004

Related U.S. Application Data

(60) Provisional application No. 60/424,298, filed on Nov. 6, 2002.

(51) Int. Cl.
*C12N 15/82* (2006.01)
*A01H 5/00* (2006.01)

(52) U.S. Cl. .................. 536/24.1; 800/298; 435/320.1

(58) Field of Classification Search .............. 536/24.1; 435/320.1; 800/298
See application file for complete search history.

(56) References Cited

U.S. PATENT DOCUMENTS 6,225,529 B1 * 5/2001 Lappegard et al. ......... 800/287

FOREIGN PATENT DOCUMENTS

| EP | 1 209228 A2 | 5/2002 |
|---|---|---|
| WO | 03/008540 A2 | 1/2003 |

OTHER PUBLICATIONS

Kim, Y.et al. A 20 nucleotide upstream element is essential for the nopaline synthase (nos) promoter activity. Plant Mol Biol. Jan. 1994;24(1):105-17.*
Lappegard K. sequence alignment with Sequence 4 from U.S. Appl. No. US/09377648, filed Aug. 19, 1999 and issued as U.S. Pat. No. 6,225,529 May 1, 2001.*
Shen Q. et al. Modular nature of abscisic acid (ABA) response complexes: composite promoter units that are necessary and sufficient for ABA induction of gene expression in barley. Plant Cell. Jul. 1996;8(7):1107-19.*
Fiedler U. et al. A complex ensemble of cis-regulatory elements controls the expression of a *Vicia faba* non-storage seed protein gene. Plant Mol Biol. Jul. 1993;22(4):669-79.*
Guilfoyle, T.J. et al., "The ARF family of transcription factors and their role in plant hormone-responsive trancription"; Cell.Mol.Life Sci. 54 (1998) 619-627; Birkhauser Vertag, Basel.
Reddy, A.S.N. et al.; "Molecular cloning and sequencing of a cDNA for an auxin-repressed mRNA: correlation between fruit growth repression of the auxin-regulated gene"; Plant Molecular Biology 14(2): 127-136 (1990); Kluwer Academic Publishers, Belgium.
Stafstrom, Joel P., et al.; "Dormancy-associated gene expression in pea axillary buds."1 Planta (1998) 205:547-552; Springer-Verlag.
Steiner et al.; "Two novel genes are differentially expressed during early germination of the male gametophyte of *Nicotiana tabacum*"; Biochima et Biophysica Acta.; Jan. 27, 2003, vol. 1635, pp. 123-133.
Kasuga, M., et al.; "Improving plant drought, salt, and freezing tolerance by gene transfer of a single stress-inducible transcription factor"; Nature Biotechnology (1999) 17:287-291.
Yamaguchi-Shinozaki, K., et al.; "A Novel cis-Acting Element in an *Arabidopsis* Gene Is Involved in Responsiveness to Drought, Low-Temperature, or High-Salt Stress"; The Plant Cell (1994) 6:251-264.
Baker, S.S., et al.; "The 5'-region of *Arabidopsis thaliana* cor15a has cis-acting elements that confer cold-, drought, and ABA-regulated gene expression"; Plant Molecular Biology (1994) 24:701-713.
Dolferus, R., et al.; "Differentual Interactions of Promoter Elements in Stress Responses of the *Arabidopsis* Adh Gene"; Plant Physiology (1994) 105:1075-1087.
Shinazaki, K., et al.; "Molecular responses to dehydration and low temperature: difference and cross-talk between two stress signaling pathways"; Current Opinion in Plant Biology (2000) 3:217-223.

* cited by examiner

*Primary Examiner*—Cynthia Collins

(57) ABSTRACT

The present invention provides compositions and methods for regulating expression of nucleotide sequences in a plant. Compositions comprise a novel nucleic acid sequence for a promoter which is induced by abiotic stress and the coding sequence natively associated with said promoter sequence. A method for expressing a heterologous nucleotide sequence in a plant using said promoter sequence is also provided. The methods comprise transforming a plant cell to contain a heterologous nucleotide sequence operably linked to the promoter of the present invention and regenerating a stably transformed plant from said transformed plant cell.

8 Claims, 2 Drawing Sheets

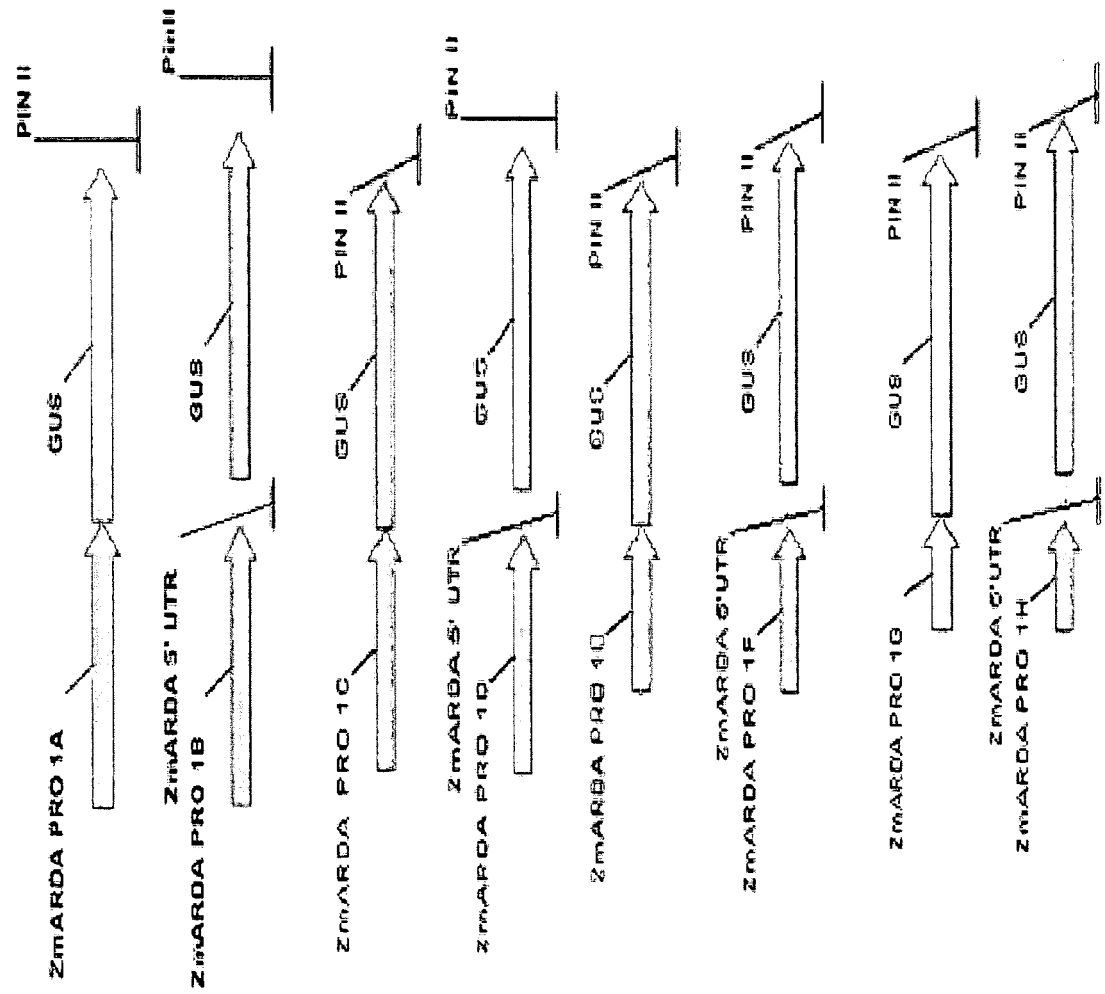

SEQUENCE LISTING

```
<160> NUMBER OF SEQ ID NOS: 9

<210> SEQ ID NO 1
<211> LENGTH: 1512
<212> TYPE: DNA
<213> ORGANISM: Zea mays
<220> FEATURE:
<221> NAME/KEY: misc_feature
<222> LOCATION: (137)...(143)
<223> OTHER INFORMATION: AuxRR-core
<220> FEATURE:
<221> NAME/KEY: CAAT_signal
<222> LOCATION: (189)...(193)
<223> OTHER INFORMATION: Also at 1280-1283
<220> FEATURE:
<221> NAME/KEY: misc_binding
<222> LOCATION: (357)...(363)
<223> OTHER INFORMATION: DPBFCOREDCDC3
<220> FEATURE:
```

```
<221> NAME/KEY: misc_feature
<222> LOCATION: (545)...(550)
<223> OTHER INFORMATION: ABRE
<220> FEATURE:
<221> NAME/KEY: misc_binding
<222> LOCATION: (565)...(570)
<223> OTHER INFORMATION: MYB binding
<220> FEATURE:
<221> NAME/KEY: misc_feature
<222> LOCATION: (704)...(709)
<223> OTHER INFORMATION: CATATGGMSAUR
<220> FEATURE:
<221> NAME/KEY: misc_feature
<222> LOCATION: (746)...(752)
<223> OTHER INFORMATION: AuxRR-core
<220> FEATURE:
<221> NAME/KEY: misc_binding
<222> LOCATION: (763)...(769)
<223> OTHER INFORMATION: DPBFCOREDCDC3
<220> FEATURE:
<221> NAME/KEY: misc_binding
<222> LOCATION: (792)...(796)
<223> OTHER INFORMATION: ASF1MOTIFCAMV
<220> FEATURE:
<221> NAME/KEY: misc_binding
<222> LOCATION: (1011)...(1016)
<223> OTHER INFORMATION: ARFAT
<220> FEATURE:
<221> NAME/KEY: TATA_signal
<222> LOCATION: (1114)...(1119)
<220> FEATURE:
<221> NAME/KEY: TATA_signal
<222> LOCATION: (1167)...(1172)
<220> FEATURE:
<221> NAME/KEY: TATA_signal
<222> LOCATION: (1170)...(1176)
<220> FEATURE:
<221> NAME/KEY: TATA_signal
<222> LOCATION: (1171)...(1176)
<220> FEATURE:
<221> NAME/KEY: misc_feature
<222> LOCATION: (1245)...(1255)
<223> OTHER INFORMATION: ABADESI2
<220> FEATURE:
<221> NAME/KEY: misc_feature
<222> LOCATION: (1246)...(1254)
<223> OTHER INFORMATION: CE3
<220> FEATURE:
<221> NAME/KEY: misc_feature
<222> LOCATION: (1390)...(1396)
<223> OTHER INFORMATION: TATC-box
<220> FEATURE:
<221> NAME/KEY: misc_feature
<222> LOCATION: (1480)...(1484)
<223> OTHER INFORMATION: CGTCA-motif

<400> SEQUENCE: 1
gtaatacgac tcactatagg gcacgcgtgg tcgacggccc gggctggtaa aataaaaaaa    60
aataatcgtg ccaggtcagg ccaacactat gtgccgaggc tacaacccaa gcatcgcacg   120
acgctcgtgg cgggttggtc cagtgactat taaatgggtc gtgcctcggg tcggctcgcc   180
agaaacagcc aatttggtca tctataccct cgcacgataa tgatggtcct cacctcagtt   240
gccaccacct cgttcgccat tctacttctt ttctctcccc cctcatgcct ccacccgtgc   300
caccccattc tcgacagagg gcgtaggagc aagcgtctcc tccccgtatt cgtccaacac   360
cagccacgac accgactcac gtagtggcta ttgcacgtcc acgaggacgt ttaacatcat   420
gcgtgcacca tcgtttttcc cgatgtcgga cgtcccgttc gtattccctg ccttcgccct   480
gttcttccac cccaacctgc tgcccccgac cacggtcgca gccacgagcc gatcgacgct   540
cgtcgacgtg ggtgcggggc aagtcggtca tgctcctggc cttttctcgt gcgtgccgtc   600
gaggaggaca tggtggcgcc tgccacgctt aggttatctt ggcgatgagg agcccaggtc   660
```

-continued

```
tgagatattg gacaaccaag gcccgtagcg tgacaacagt cagcatatgc tacggagttg      720
gtggtggtgt tgtgtcgctt cggcgggtcc agggctggga agacactcgc attctctcgc      780
ccttctcgga ttgacggctg gtgcgggtgc ctctcggttt ggagctgctc cggctaagct      840
tctttctccg cttgcatgct ctctccctat atatctagcg gtatactacc tatgtcgcct      900
ccagatgacc aggtcttcgt cgtgtccttc ggcaacgaac atgtatgctc gtctcttccc      960
ttcccctcct gctctacgaa accttggaag tggaggagac gagagatgga tgtctctgat     1020
ttgttgccta tggtacatgt gcgtttataa aaaatattat gccaagagtg gagacaacaa     1080
ataaaaaatc ttaaaatctt tttgatagat aatttatatg ggtattattg tgagtcgtcg     1140
caagtcacgg ttaaccgact agtaattatt aatatagcgc taggtaaaca gtacatacag     1200 atattttag aagtggatac gccatggatg gcgctgaaaa ggagggacgc gtggcgggct     1260
ttgaggggaa agggcgagcc aattcgtctt ccaacgcgac cccatctgtc tgatcggatt     1320 gggttgggc ctgggggtag gataatatct tggcctgggt cgtccgaagg atccatctag     1380
ttcaacaagt atccaaggcc agagatacgg ggcccggcgc cagtccggtt ttttttggt     1440 ttgattaaaa aaaaggttcc attcttatct actttgctgc gtcatcgctg ggtggtctca     1500
gacggacctg ca                                                          1512
```

<210> SEQ ID NO 2
<211> LENGTH: 354
<212> TYPE: DNA
<213> ORGANISM: Zea mays
<220> FEATURE:
<221> NAME/KEY: CDS
<222> LOCATION: (1)...(354)

<400> SEQUENCE: 2

```
atg ctg gac aag ctg tgg gac gac gtg gtg gcc ggg cct cgc ccg gag      48
Met Leu Asp Lys Leu Trp Asp Asp Val Val Ala Gly Pro Arg Pro Glu
 1               5                  10                  15 acg ggc ctc gag aag ctc cgc aag gcc acc acc gcc cgc ccg ctc gtc      96
Thr Gly Leu Glu Lys Leu Arg Lys Ala Thr Thr Ala Arg Pro Leu Val
             20                  25                  30 atc aac aaa gac gcg gac ggc ggc agc tac aag cgg gcg cag tcg atg     144
Ile Asn Lys Asp Ala Asp Gly Gly Ser Tyr Lys Arg Ala Gln Ser Met
         35                  40                  45 ccg tcg acc ccg acg acg ccg gtg acg ccg tcg tcg tcg tcg tcg         192
Pro Ser Thr Pro Thr Thr Pro Val Thr Pro Ser Ser Ser Ser Ser
     50                  55                  60 acg acg ccg cgc ggc gcc ggc aac gtg tgg cgc agc gtc ttc cac ccg     240
Thr Thr Pro Arg Gly Ala Gly Asn Val Trp Arg Ser Val Phe His Pro
 65                  70                  75                  80 ggg agc aac ctg gcc acc aag ggc atg ggc gcc aac ctc ttc gac cgg     288
Gly Ser Asn Leu Ala Thr Lys Gly Met Gly Ala Asn Leu Phe Asp Arg
                 85                  90                  95 ccg cag ccc aac tcc ccc acc gtc tac gac tgg ctc tac agc gac gag     336
Pro Gln Pro Asn Ser Pro Thr Val Tyr Asp Trp Leu Tyr Ser Asp Glu
            100                 105                 110 acc agg agc aac cac cgc                                             354
Thr Arg Ser Asn His Arg
        115
```

<210> SEQ ID NO 3
<211> LENGTH: 118
<212> TYPE: PRT
<213> ORGANISM: Zea mays

<400> SEQUENCE: 3

Met Leu Asp Lys Leu Trp Asp Asp Val Val Ala Gly Pro Arg Pro Glu
1               5                   10                  15

Thr Gly Leu Glu Lys Leu Arg Lys Ala Thr Thr Ala Arg Pro Leu Val
            20                  25                  30

Ile Asn Lys Asp Ala Asp Gly Gly Ser Tyr Lys Arg Ala Gln Ser Met
        35                  40                  45

Pro Ser Thr Pro Thr Thr Pro Val Thr Pro Ser Ser Ser Ser Ser Ser
    50                  55                  60

Thr Thr Pro Arg Gly Ala Gly Asn Val Trp Arg Ser Val Phe His Pro
65                  70                  75                  80

Gly Ser Asn Leu Ala Thr Lys Gly Met Gly Ala Asn Leu Phe Asp Arg
                85                  90                  95

Pro Gln Pro Asn Ser Pro Thr Val Tyr Asp Trp Leu Tyr Ser Asp Glu
            100                 105                 110

Thr Arg Ser Asn His Arg
        115

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
tggtggcctt gcggagcttc tc                                      22

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
gtaatacgac tcactatagg gc                                      22

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
actatagggc acgcgtggt                                          19

<210> SEQ ID NO 7
<211> LENGTH: 1297
<212> TYPE: DNA
<213> ORGANISM: Zea mays
<220> FEATURE:
<221> NAME/KEY: promoter
<222> LOCATION: (1)...(1297)
<223> OTHER INFORMATION: Truncated promoter for constructs 1C and 1D of
                        Figure 2

<400> SEQUENCE: 7
gataatgatg gtcctcacct cagttgccac cacctcgttc gccattctac ttctttctc    60 tcccccctca tgcctccacc cgtgccaccc cattctcgac agagggcgta ggagcaagcg  120

-continued

```
tctcctcccc gtattcgtcc aacaccagcc acgacaccga ctcacgtagt ggctattgca        180
cgtccacgag gacgtttaac atcatgcgtg caccatcgtt ttccccgatg tcggacgtcc        240
cgttcgtatt ccctgccttc gccctgttct tccaccccaa cctgctgccc ccgaccacgg        300
tcgcagccac gagccgatcg acgctcgtcg acgtgggtgc ggggcaagtc ggtcatgctc        360
ctggcctttc tccgtgcgtg ccgtcgagga ggacatggtg gcgcctgcca cgcttaggtt        420
atcttggcga tgaggagccc aggtctgaga tattggacaa ccaaggcccg tagcgtgaca        480
acagtcagca tatgctacgg agttggtggt ggtgttgtgt cgcttcggcg ggtccagggc        540
tgggaagaca ctcgcattct ctcgcccttc tcggattgac ggctggtgcg ggtgcctctc        600
ggtttggagc tgctccggct aagcttcttt ctccgcttgc atgctctctc cctatatatc        660
tagcggtata ctacctatgt cgcctccaga tgaccaggtc ttcgtcgtgt ccttcggcaa        720
cgaacatgta tgctcgtctc ttcccttccc ctcctgctct acgaaacctt ggaagtggag        780
gagacgagag atggatgtct ctgatttgtt gcctatggta catgtgcgtt tataaaaaat        840
attatgccaa gagtggagac aacaaataaa aaatcttaaa atcttttga tagataattt        900 atatgggtat tattgtgagt cgtcgcaagt cacggttaac cgactagtaa ttattaatat        960
agcgctaggt aaacagtaca tacagatatt tttagaagtg gatacgccat ggatggcgct       1020
gaaaaggagg gacgcgtggc gggctttgag ggggaagggc gagccaattc gtcttccaac       1080
gcgaccccat ctgtctgatc ggattgggtt ggggcctggg ggtaggataa tatcttggcc       1140
tgggtcgtcc gaaggatcca tctagttcaa caagtatcca aggccagaga tacggggccc       1200
ggcgccagtc cggttttttt ttggtttgat taaaaaaaag gttccattct tatctacttt       1260
gctgcgtcat cgctgggtgg tctcagacgg acctgca                                1297
```

```
<210> SEQ ID NO 8
<211> LENGTH: 889
<212> TYPE: DNA
<213> ORGANISM: Zea mays
<220> FEATURE:
<221> NAME/KEY: promoter
<222> LOCATION: (1)...(889)
<223> OTHER INFORMATION: Truncated promoter for constructs 1E and 1F of
                        Figure 2

<400> SEQUENCE: 8
cacgcttagg ttatcttggc gatgaggagc ccaggtctga gatattggac aaccaaggcc         60
cgtagcgtga caacagtcag catatgctac ggagttggtg gtggtgttgt gtcgcttcgg        120
cgggtccagg gctgggaaga cactcgcatt ctctcgccct tcggattgac ggctggtg         180 cggtgcctc tcggtttgga gctgctccgg ctaagcttct ttctccgctt gcatgctctc        240
tccctatata tctagcggta tactacctat gtcgcctcca gatgaccagg tcttcgtcgt        300
gtccttcggc aacgaacatg tatgctcgtc tcttcccttc cctcctgct ctacgaaacc       360 ttggaagtgg aggagacgag agatggatgt ctctgatttg ttgcctatgg tacatgtgcg       420
tttataaaaa atattatgcc aagagtggag acaacaaata aaaaatctta aaatctttt         480 gatagataat ttatatgggt attattgtga gtcgtcgcaa gtcacggtta accgactagt        540
aattattaat atagcgctag gtaaacagta catacagata tttttagaag tggatacgcc        600
atggatggcg ctgaaaagga gggacgcgtg gcgggctttg aggggaaagg gcgagccaat       660
tcgtcttcca acgcgacccc atctgtctga tcggattggg ttggggcctg ggggtaggat       720
aatatcttgg cctgggtcgt ccgaaggatc catctagttc aacaagtatc caaggccaga      780
```

```
gatacggggc ccggcgccag tccggttttt ttttggtttg attaaaaaaa aggttccatt    840
cttatctact ttgctgcgtc atcgctgggt ggtctcagac ggacctgca                889

<210> SEQ ID NO 9
<211> LENGTH: 586
<212> TYPE: DNA
<213> ORGANISM: Zea mays
<220> FEATURE:
<221> NAME/KEY: promoter
<222> LOCATION: (1)...(586)
<223> OTHER INFORMATION: Truncated promoter for constructs 1G and 1H of
                        Figure 2

<400> SEQUENCE: 9
cttcggcaac gaacatgtat gctcgtctct tcccttcccc tcctgctcta cgaaaccttg     60
gaagtggagg agacgagaga tggatgtctc tgatttgttg cctatggtac atgtgcgttt    120
ataaaaaata ttatgccaag agtggagaca acaaataaaa aatcttaaaa tcttttttgat   180 agataattta tatgggtatt attgtgagtc gtcgcaagtc acggttaacc gactagtaat    240
tattaatata gcgctaggta aacagtacat acagatattt ttagaagtgg atacgccatg    300
gatggcgctg aaaaggaggg acgcgtggcg ggctttgagg ggaaagggcg agccaattcg    360
tcttccaacg cgacccatc tgtctgatcg gattgggttg gggcctgggg gtaggataat    420
atcttggcct gggtcgtccg aaggatccat ctagttcaac aagtatccaa ggccagagat    480
acggggcccg gcgccagtcc ggttttttttt tggtttgatt aaaaaaaagg ttccattctt    540
atctactttg ctgcgtcatc gctgggtggt ctcagacgga cctgca                  586
```

AUXIN-REPRESSED, DORMANCY-ASSOCIATED PROMOTER AND USES THEREOF

CROSS-REFERENCE TO RELATED APPLICATIONS

This application claims the benefit of U.S. Provisional Application No. 60/424,298 filed Nov. 6, 2002.

FIELD OF THE INVENTION

The present invention relates to the field of plant molecular biology, more particularly to regulation of gene expression in plants.

BACKGROUND OF THE INVENTION

Expression of a heterologous DNA sequence in a plant host is dependent upon the presence of an operably-linked promoter that is functional within the plant host. Choice of the promoter sequence will determine when and where within the plant the heterologous DNA sequence is expressed. Where continuous expression is desired throughout the cells of a plant, a constitutive promoter is utilized. Where gene expression in response to a stimulus is desired, an inducible promoter is the regulatory element of choice. Where expression in a specific tissue or organ is desired, a tissue-preferred promoter is used. Such a tissue-preferred promoter may be inducible. Expression during a particular developmental stage may be achieved with a developmentally-regulated promoter. Additional regulatory sequences upstream and/or downstream from the core promoter sequence can be included in expression cassettes of transformation vectors to bring about varying levels of expression of heterologous nucleotide sequences in a transgenic plant. See, for example, U.S. Pat. No. 5,850,018. Regulatory sequences may also be useful in controlling temporally- and/or spatially-differentiated expression of endogenous DNA.

In grain crops of agronomic importance, seed formation is the ultimate goal of plant development. Seeds are harvested for use in food, feed, and industrial products. The utility and value of those seeds are determined by the quantity and quality of protein, oil, and starch contained therein. In turn, the quality and quantity of seed produced may be affected by environmental conditions at any point prior to fertilization through seed maturation. In particular, stress at or around the time of fertilization may have substantial impact on seed development.

Stresses to plants may be caused by both biotic and abiotic agents. For example, biotic causes of stress include infection with a pathogen, insect feeding, parasitism by another plant such as mistletoe, and grazing by ruminant animals. Abiotic stresses include, for example, excessive or insufficient available water, insufficient light, temperature extremes, synthetic chemicals such as herbicides, excessive wind, extremes of soil pH, limited nutrient availability, and air pollution. Yet plants survive and often flourish, even under unfavorable conditions, using a variety of internal and external mechanisms for avoiding or tolerating stress. Plants' physiological responses to stress reflect changes in gene expression.

While manipulation of stress-induced genes may play an important role in improving plant tolerance to stresses, it has been shown that constitutive expression of stress-inducible genes has a severe negative impact on plant growth and development when the stress is not present. (Kasuga et al., (1999) Nature Biotechnology 17(3):287-291) Therefore, there is a need in the art for promoters driving expression which is temporally- and/or spatially-differentiated, to provide a means to control and direct gene expression in specific cells or tissues at critical times, especially to provide stress tolerance or avoidance.

In particular, drought and/or density stress of maize often results in reduced yield, typically from plant failure to set and fill seed in the apical portion of the ear, a condition known as "tip kernel abortion" or colloquially as "nosing back." To stabilize plant development and grain yield under unfavorable environments, manipulation of hormones and carbon supply to the developing ear and its kernels is of interest. Thus there is a need for promoters which drive gene expression in female reproductive tissues under abiotic stress conditions.

Improvement of crop plants with multiple transgenes is of increasing interest. This is sometimes known as gene "stacking" and provides opportunities for the manipulation of plant physiology to meet a variety of challenges during the lifecycle of the transformed plant. For example, a single maize hybrid may comprise recombinant DNA constructs conferring not only insect resistance, in the transformed plant's ability to produce an insecticidal toxin derived from *Bacillus thuringiensis*, but also resistance to a specific herbicide, through incorporation of a *Streptomyces hygroscopicus* gene that detoxifies glufosinate. Importantly, appropriate regulatory sequences are needed to drive the desired expression of each of these or other transgenes of interest. Furthermore, it is important that regulatory elements be distinct from each other. Concerns associated with the utilization of similar regulatory sequences to drive expression of multiple genes include, but are not restricted to: (a) pairing along homologous regions, crossing-over and loss of the intervening region either within a plasmid prior to integration, or within the plant genome, post-integration; (b) hairpin loops caused by two copies of the sequence in opposite orientation adjacent to each other, again with possibilities of excision and loss of these regulatory regions; (c) competition among different copies of the same promoter region for binding of promoter-specific transcription factors or other regulatory DNA-binding proteins.

Thus, there is a continuing need for promoters which will drive gene expression in the appropriate tissues, at the proper time, to the desired degree, and in response to the relevant stimuli.

SUMMARY OF THE INVENTION

Embodiments of the invention include compositions and methods for regulating expression of one or more heterologous nucleotide sequences in a plant. Embodiments comprise novel promoter sequences that preferentially initiate transcription of operably linked polynucleotides in response to abiotic stress. Such embodiments may comprise expression in developing female florets of *Zea mays*, as well as in other tissues and in other species. Further compositions of the invention comprise the nucleotide sequence set forth in SEQ ID NO:1, and operable fragments and variants thereof. The compositions of the invention further comprise functional promoter sequences having at least 75% identity to the sequence set forth in SEQ ID NO:1, and functional promoter sequences that hybridize under stringent conditions to a complement of SEQ ID NO: 1. In one embodiment, an expression cassette comprises a promoter sequence of the invention operably linked to a polynucleotide of interest, wherein said promoter sequence drives expression of the linked polynucleotide in a plant cell. Further embodiments of the invention include vectors containing the expression cassette, transformed plant cells, transformed plants, and transformed seeds comprising the novel promoter sequences of the invention.

In another embodiment, methods for expressing a polynucleotide of interest in a plant are provided. The methods comprise stably incorporating into the genome of a plant cell an expression cassette comprising a promoter sequence of the invention operably linked to a polynucleotide of interest, wherein the promoter is capable of initiating transcription of the linked polynucleotide in a plant cell. The transformed plant cell can be regenerated to obtain a transformed plant. In a further embodiment, the methods provide a means for expressing a selected polynucleotide in developing female florets under conditions of abiotic stress, such as under drought and/or density stress. Such expression may modulate the development of the female inflorescence of the transformed plant under conditions of stress.

BRIEF DESCRIPTION OF THE FIGURES

FIG. 2 is a schematic drawing representing promoter deletion constructs.

DETAILED DESCRIPTION OF THE INVENTION

Figure 1:
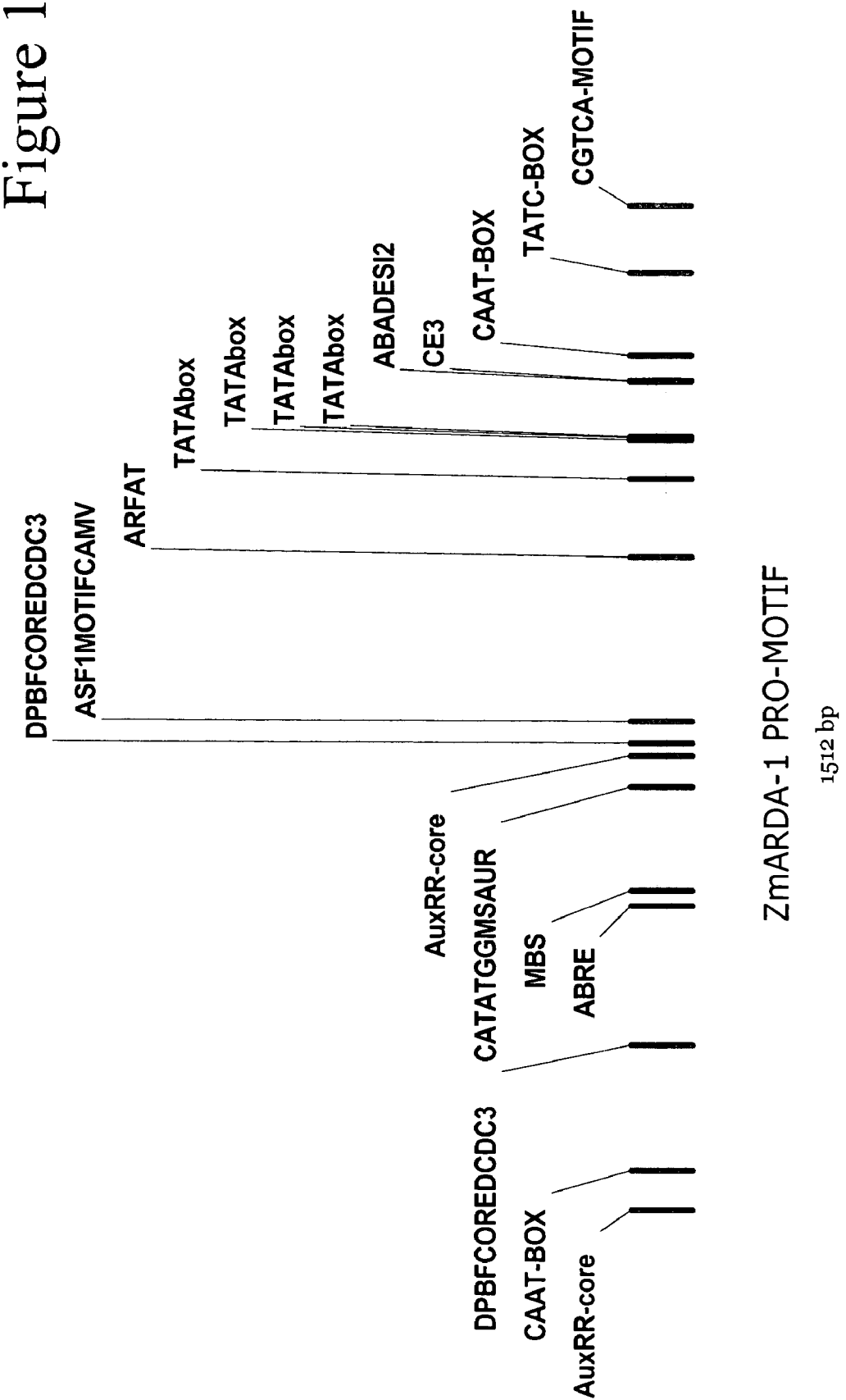
FIG. 1 is a schematic drawing which shows the relative locations of certain recognition sequences within the claimed promoter region. These motifs are also identified as special features in the sequence listing for SEQ ID NO: 1.

In accordance with the invention, nucleotide sequences are provided that comprise transcription initiation regions associated with stress-induced gene expression. Thus, the compositions of the present invention comprise a novel nucleotide sequence for a plant promoter, more particularly a promoter which preferentially initiates transcription in *Zea mays* in response to abiotic stress, including but not limited to the stresses of drought or density. Such expression occurs in developing female florets of *Zea mays* and may occur in other plant tissues and in other species.

Also provided is a sequence for a stress-responsive *Zea mays* gene, ZmARDA-1 (auxin-repressed, dormancy-associated). Expression differentials among and within developing female florets suggest that increased ZmARDA-1 signal is an indicator of floret abortion.

By "recombinant expression cassette" or "expression cassette" is meant a nucleic acid construct, generated recombinantly or synthetically, comprising a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the expression cassette portion of an expression vector includes, among other sequences, a promoter and a nucleic acid to be transcribed.

By "heterologous nucleotide sequence" is intended a sequence that is not naturally occurring with the promoter sequence. While this nucleotide sequence is heterologous to the promoter sequence, it may be homologous (native) or heterologous (foreign) to the plant host.

The term "isolated" refers to material, such as a nucleic acid or a protein, which is substantially free from components that normally accompany or interact with it as found in its naturally occurring environment. The isolated material optionally comprises material not found with the material in its natural environment. Alternatively, if the material is in its natural environment, the composition of the material and/or the location of the material within the cell has been altered by human intervention. Such alteration can be performed on the material within or removed from its natural state. For example, a naturally-occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., WO 93/22443. The isolated nucleic acid may also be produced by the synthetic re-arrangement ("shuffling") of a part or parts of one or more allelic forms of the gene of interest. Likewise, a naturally-occurring nucleic acid (including, for example, a promoter) becomes isolated if it is introduced by means of human intervention to a locus of the genome not native to that nucleic acid. Nucleic acids which are "isolated" as defined herein, are also referred to as "heterologous" nucleic acids.

By "operably linked" is meant that a functional linkage exists between a promoter and a second sequence, wherein the promoter sequence initiates and mediates transcription of the DNA corresponding to the second sequence. Generally, operably linked means that the nucleic acid sequences being linked are contiguous.

As used herein, the term "plant" includes reference to whole plants and their components, including organs (e.g., leaves, stems, roots, etc.), seeds and plant cells, and progeny of same. Plant cell, as used herein includes, without limitation, cells derived from seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Helianthus, Lactuca, Bromus, Asparagus, Antirrhinum, Heterocallis, Nemesis, Pelargonium, Panicum, Pennisetum, Ranunculus, Senecio, Salpiglossis, Cucumis, Browallia, Glycine, Pisum, Phaseolus, Lolium, Oryza, Avena, Hordeum, Secale, Allium,* and *Triticum.* A particularly preferred plant is *Zea mays.*

By "plant population density," "population density," "plant density" or simply "density" is meant the number of individual plants per unit of land area. Population density of hybrid *Zea mays* at harvest is expected to be less than population density at planting and typically ranges from 28,000 to 35,000 plants per acre. The optimum density varies among hybrids and is also dependent upon numerous environmental factors, including, but not limited to, soil fertility and available moisture.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate.

A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*.

The auxin-repressed, dormancy-associated promoter of the present invention comprises a number of known upstream recognition sequences, many of which are controlled by the known stress-responsive hormone, ABA. As shown in FIG. 1 and in SEQ ID NO: 1, these recognition sequences include the following:

AuxRR-core (two sites), a cis-acting regulatory element involved in auxin responsiveness.

CAAT box (two sites), a common cis-acting element in promoter and enhancer regions.

DPBFCOREDCDC3 (two sites), similar to the core sequence for the binding site of the bZIP transcription factors DPBF-1 and DPBF-2 within the promoter of the embryo-specific, ABA-inducible Dc3 gene from *Daucus carota*. A bZIP transcription factor in *Arabidopsis* is encoded by the abscisic acid response gene ABI5.

ABRE, a cis-acting element involved in abscisic acid responsiveness.

MBS, a MYB binding site.

CATATGGMSAUR, an element of the SAUR (Small Auxin-Up RNA) 15A gene promoter in soybean, involved in auxin responsiveness ASF1MOTIFCAMV, a TGACG motif found in many promoters and involved in transcriptional activation of several genes by auxin and/or salicylic acid; may be relevant to light regulation; binding site for ASF-1 in the CaMV 35S promoter, and for the TGA1a binding protein in tobacco.

ARFAT, an auxin-response-factor binding site found in the promoters of primary/early auxin-response genes of *Arabidopsis*; binding site of *Arabidopsis* ARF1. The sequence is also found in the NDE element of the *Glycine max* SAUR 15A promoter and in the D1 or D4 element in the *Glycine max* GH3 promoter.

Elements positioned downstream, or 3' to the TATA box, include:

ABADESI2, an element which mediates response to ABA and is related to desiccation; expression is directed to seeds.

CE3, a cis-acting element involved in ABA and VP1 responsiveness.

TATC-box, a cis-acting element involved in gibberellin responsiveness.

CGTCA-motif, a cis-acting element involved in methyl-jasmonate responsiveness.

It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue and temporal expression of the coding sequence, enhancers and the like. It is further recognized that regions of SEQ ID NO: 1 outside of the identified regulatory elements may tolerate substantial modification without effect on promoter activity. In addition, the promoter elements which enable desired expression can be identified, isolated, and used with other core promoters.

In addition to the unmodified ZmARDA-1 promoter sequence, SEQ ID NO: 1, the current invention includes functional derivatives of this sequence. For example, based on the information provided herein with respect to functional elements, one of skill in the art could derive functional promoters by deleting or modifying non-essential portions of the sequence without disrupting the essential functional elements. One efficient means for preparing such derivatives comprises introducing mutations into the sequences of the invention. Such mutants may potentially have enhanced or altered function relative to the native sequence or alternatively, may be silent with regard to function. Such changes could be made, for example, by site-specific mutagenesis techniques, as described below.

Mutagenesis may be carried out at random and the mutagenized sequences screened for function in a trial-and-error procedure. Alternatively, particular sequences which provide the ZmARDA-1 promoter with desirable expression characteristics can be introduced into other related or non-related sequences via mutation. Similarly, non-essential elements may be deleted without significantly altering promoter function. It further is contemplated that one could mutagenize promoter sequences in order to enhance their utility in expressing transgenes in a particular species, for example, in maize.

Mutagenesis may be performed in accordance with any of the techniques known in the art, such as, but not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double-stranded plasmids also are routinely employed in site directed mutagenesis which eliminates the step of transferring the gene of interest from a plasmid to a phage.

Site-directed mutagenesis in accordance herewith is typically performed by first obtaining a single-stranded vector or melting apart two strands of a double-stranded vector which includes within it the sequence of interest, such as the ZmARDA-1 promoter. An oligonucleotide primer bearing the desired mutated sequence is prepared, generally synthetically. This primer is then annealed with the single-sided vector, and subjected to DNA polymerizing enzymes such as the *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and cells are selected which include recombinant vectors bearing the mutated sequence arrangement. Vector DNA can then be isolated from these cells and used for plant transformation. A genetic selection scheme was devised by Kunkel et al. (PNAS 84(14):4865-4869, 1987) to enrich for clones incorporating mutagenic oligonucleotides. Alternatively, the use of polymerase chain reaction (PCR) with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (Cell Regulation 1(12):965-973, 1990) and Upender et al (Biotechniques 18(1):29-30, 32, 1995) provide two examples of such protocols. PCR employing a thermostable ligase in addition to a therostmable polymerase also may be used to incorporate a phosphorylated mutagenic oligonucleotide into an amplified DNA fragment that may then be cloned into an appropriate cloning or expression vector.

The preparation of sequence variants of the selected promoter using site-directed mutagenesis is provided as a means of producing potentially useful species and is not meant to be limiting, as there are other ways in which sequence variants of DNA sequences may be obtained. For example, recombinant vectors encoding the desired promoter sequence may be treated with mutagenic agents to obtain sequence variants.

One efficient, targeted means for preparing mutagenized promoters relies upon the identification of putative regulatory elements within the target sequence. This can be initiated by comparison with, for example, promoter sequences known to be expressed in a similar manner. Sequences which are shared among elements with similar functions or expression patterns are likely candidates for the binding of transcription factors and are thus likely elements which confer expression patterns. Confirmation of these putative regulatory elements can be achieved by deletion analysis of each putative regulatory region followed by assay of a reporter gene which is operably linked to each construct, to evaluate function. As such, once a starting promoter or intron sequence is provided, any of a number of different functional deletion mutants of the starting sequence could be readily prepared.

As indicated above, deletion mutants of the ZmARDA-1 promoter of the invention also could be randomly prepared and then assayed. With this strategy, a series of constructs are prepared, each containing a different portion of the clone (a subclone), and these constructs are then screened for activity. A suitable means for screening for activity is to operably link a deleted promoter construction to a selectable or screenable marker, and to isolate only those cells or tissues or plants which express the marker gene. In this way, a number of different, deleted promoter constructs are identified which still retain the desired, or even enhanced, activity. See, for example, FIG. 2 and SEQ ID NOS: 7, 8, and 9, which provide truncated promoter sequences in appropriate screening constructs. The smallest segment which is required for activity is thereby identified through comparison of the selected constructs. This segment may then be used for the construction of vectors for the expression of heterologous genes.

The isolated promoter sequence of the present invention can be modified to provide for a range of expression levels of the heterologous nucleotide sequence. Less than the entire promoter region can be utilized and the ability to drive expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence; however, specific elements and combinations of elements, such as those involved in temporal-, developmental- or tissue-specificity, or in response to environmental factors, may be needed to achieve the desired expression.

Also, differences in the relative strength of expression of a promoter may exist either within or between species, wherein a promoter may provide optimum levels of expression of one gene in a certain cell type or species, but may be either too strong or too weak to provide the desired level of expression of a different gene in a certain cell type or species.

It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

Methods for isolation of promoter regions are well known in the art. Exemplary methods are described in U.S. patent application Ser. No. 09/387,720 filed Aug. 30, 1999, and in U.S. Pat. No. 6,528,704 issued Mar. 4, 2003, both of which are herein incorporated by reference.

Certain embodiments of the invention comprise the sequence set forth in SEQ ID NO: 1.

The promoter region of the invention may be isolated from any plant, including, but not limited to maize (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanut (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), oat (*Avena sativa*), vegetables, ornamentals, and conifers. Preferably, plants include maize, soybean, sunflower, safflower, canola, wheat, rye, alfalfa, and sorghum.

The *Zea mays* promoter sequence of the invention can be used to isolate corresponding sequences from other organisms, particularly from other plants, more particularly from other monocotyledonous plants. Methods such as PCR, hybridization, and the like can be used to identify such sequences based on their similarity to a sequence set forth herein. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the sequences of the invention. For example, an entire sequence disclosed herein, or one or more portions thereof, may be used as a probe capable of specifically hybridizing to corresponding sequences. To achieve specific hybridization under a variety of conditions, such probes include sequences that are distinctive and are preferably at least about 10 nucleotides in length, and most preferably at least about 20 nucleotides in length. The well-known process of polymerase chain reaction (PCR) may be used to isolate or amplify additional sequences from a chosen organism or as a diagnostic assay to determine the presence of corresponding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.). see also Innis et al., eds., (1990) *PCR Protocols, A Guide to Methods and Applications*, Academic Press). Methods for preparation of probes for hybridization and for construction of cDNA and genomic libraries are generally known in the art and are disclosed in Sambrook et al., supra.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are target-sequence-dependent and will differ with the structure of the polynucleotide. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See also Sambrook et al., supra. Thus, isolated sequences that retain the promoter function of the invention and hybridize under stringent conditions to a complement of any of the sequences disclosed herein, or to fragments of such complements, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99% or more homologous with the disclosed sequence. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99% or more sequence identity.

Sequences isolated based on their sequence identity to the entire promoter sequence set forth herein or to fragments thereof are encompassed by the present invention.

One embodiment of the invention comprises an isolated polynucleotide natively associated with and capable of driving expression of a nucleotide sequence that is at least 85%, 90%, 91%, 92%, 93%, 94%, 95%, 96%, 97%, 98%, or 99% identical to the coding sequence of *Zea mays* ZmARDA-1, SEQ ID NO: 2. By "natively associated" is intended that the promoter sequence has not been operably linked to the nucleotide sequence by human intervention. Another embodiment of the invention includes a method for identifying stress-responsive, tissue-preferred promoters by identifying polynucleotides encoding polypeptides having at least 85%, 90%, 91%, 92%, 93%, 94%, 95%, 96%, 97%, 98%, or 99% identity to the polypeptide encoded by *Zea mays* ZmARDA-1, SEQ ID NO: 2.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Genetics Computer Group (GCG®) set of programs, Accelrys, Inc., San Diego, Calif. The CLUSTAL program is well described by Higgins and Sharp, *Gene* 73: 237-244 (1988); Higgins and Sharp, CABIOS 5: 151-153 (1989); Corpet, et al., Nucleic Acids Research 16: 10881-90 (1988); Huang, et al., Computer Applications in the *Biosciences* 8: 155-65 (1992), and Pearson, et al., Methods in Molecular Biology 24: 307-331 (1994). BLAST (Basic Local Alignment Search Tool) is described by Altschul, S. F., et al., (1993) J. Mol. Biol. 215:403-410. Unless otherwise specified, sequence comparisons herein are based on GAP alignment using default parameters. GAP default parameters include a gap creation penalty of 50, a gap extension penalty of 3, and no penalty for gaps at either end of the alignment.

Identity to the sequence of the present invention would mean a polynucleotide sequence having at least 75% sequence identity, more preferably at least 80% identity, more preferably at least 85% sequence identity, more preferably at least 90% sequence identity and most preferably at least 95% sequence identity, wherein the percent sequence identity is based on the entire promoter region as disclosed in SEQ ID NO: 1.

The invention also encompasses fragments of the sequence set forth in SEQ ID NO: 1. Fragments of a nucleotide sequence may range from at least about 20 nucleotides, to about 50 nucleotides, to about 100 nucleotides, and up to the full-length nucleotide sequence of the invention. Fragments of a nucleotide sequence may retain biological activity and hence initiate transcription of a heterologous nucleotide sequence, and may comprise elements responsible for temporal, hormonal or environmental response, and/or tissue preference. The nucleotides of such fragments will usually comprise the TATA recognition sequence of the particular promoter sequence. Such fragments can be obtained, for example, by use of restriction enzymes to cleave the naturally-occurring promoter nucleotide sequences disclosed herein; by synthesizing a nucleotide sequence from the naturally-occurring promoter DNA sequence; or through the use of PCR technology. See particularly, Mullis et al. (1987) *Methods Enzymol.* 155:335-350, and Erlich, ed. (1989) *PCR Technology* (Stockton Press, New York). Alternatively, fragments of a promoter nucleotide sequence that do not retain biological activity are useful as hybridization probes.

Variants and derivatives of the promoter nucleotide sequence disclosed herein are also encompassed by the present invention. By "variants" or "derivatives" is intended substantially similar sequences wherein one or more bases have been modified, removed or added. For nucleotide sequences, naturally-occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein, using default parameters.

Certain variant nucleotide sequences of the present invention retain biological activity (i.e. regulate transcription under conditions of environmental stress, including such regulation in developing female florets of the plant). One example of a regulatory sequence variant is a promoter formed by one or more deletions from a larger promoter. The 5' portion of a promoter up to the TATA box near the transcription start site can sometimes be deleted without abolishing promoter activity, as described by Zhu et al., *The Plant Cell* 7: 1681-89 (1995). A routine way to remove part of a DNA sequence is to use an exonuclease in combination with DNA amplification to produce unidirectional nested deletions of double-stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digestion of a clone with this enzyme produces unidirectional nested deletions. Biologically active variants also include, for example, the native promoter sequences of the invention having one or more nucleotide substitutions, deletions or insertions. Methods to assay transcriptional regulation are well known in the art. Assay methods include Northern blots, RT-PCR, and use of reporter sequences such as GUS. See, for example, Sambrook et al., supra, herein incorporated by reference.

The nucleotide sequences for the promoter of the invention, including operable fragments and variants thereof, can be provided in expression cassettes along with heterologous nucleotide sequences for expression in the plant of interest, more particularly in developing female florets of the plant under conditions of environmental stress. Such an expression cassette is provided with a plurality of restriction sites for insertion of a nucleotide sequence to be under the transcriptional regulation of a promoter. These expression cassettes are useful in the genetic manipulation of any plant to achieve a desired phenotypic response.

Genes of interest, expressed under direction of the promoter of the invention, can modulate plant development under conditions of stress, such as the development of female florets in drought conditions. This can be achieved by increasing expression of endogenous or exogenous products in the developing female florets. Alternatively, the results can be achieved by providing for a reduction of expression of one or more endogenous products.

General categories of genes of interest for the purposes of the present invention include, for example, those genes involved in information, such as Zinc fingers, those involved in communication, such as kinases, and those involved in housekeeping, such as heat shock proteins. More specific categories of transgenes include genes encoding important traits for agronomic quality, insect resistance, disease resistance, herbicide resistance, and grain characteristics. Still other categories of transgenes include genes for inducing expression of exogenous products such as enzymes, cofactors, and hormones from plants and other eukaryotes as well as from prokaryotic organisms. It is recognized that any gene of interest can be operably linked to the promoter of the invention and expressed under stress.

In a more preferred embodiment, the promoter of the instant invention modulates genes encoding proteins which act as cell cycle regulators, or which control carbohydrate metabolism or phytohormone levels, as has been shown in tobacco and canola with other tissue-preferred promoters. (Ma, Q. H., et al., (1998) *Australian Journal of Plant Physiology* 25(1): 53-59; Roeckel, P., et al., (1997) *Transgenic Research* 6(2):133-141.) For example, genes encoding isopentenyl transferase or IAA-M may be useful in modulating development of the female florets. Other important genes encode growth factors and transcription factors. Expression of selected endogenous or heterologous nucleotides under the direction of the promoter may result in continued or improved development of the female florets under adverse conditions.

Seed production may be improved by altering expression of genes that affect the response of seed growth and development during environmental stress (Cheikh-N et al., (1994) *Plant Physiol.* 106(1):45-51) and genes controlling carbohydrate metabolism to reduce seed abortion in maize (Zinselmeier et al. (1995) *Plant Physiol.* 107(2):385-391).

The nucleotide sequence operably linked to the promoter disclosed herein can be an antisense sequence for a targeted gene. By "antisense sequence" is intended a sequence that is in inverse orientation to the 5'-to-3' normal orientation of that nucleotide sequence. The antisense nucleotide sequence encodes an RNA transcript that is complementary to and capable of hybridizing with the endogenous messenger RNA (mRNA) produced by transcription of the DNA nucleotide sequence for the targeted gene. In this way, production of the native protein encoded by the targeted gene is inhibited to achieve a desired phenotypic response. Thus, for example, the promoter sequence disclosed herein can be operably linked to antisense DNA sequences to reduce or inhibit expression of a native protein in the developing female florets.

The expression cassette will also include, at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Nat. Acad. Sci. USA* 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al. (1989) *Molecular Biology of RNA*, pages 237-256; and maize chlorotic mottle virus leader (MCMV) Lommel et al. (1991) *Virology* 81:382-385. See also Della-Cioppa et al. (1987) *Plant Physiology* 84:965-968. The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments can be manipulated so as to provide for the DNA sequences in the proper orientation and, as appropriate, in the proper reading frame. Toward this end, adapters or linkers can be employed to join the DNA fragments, or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest under the control of the promoter. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al., supra.

The transformation vector, comprising the promoter sequence of the present invention operably linked to a heterologous nucleotide sequence in an expression cassette, can also contain at least one additional nucleotide sequence for a gene to be cotransformed into the organism. Alternatively, the additional sequence(s) can be provided on one or more additional transformation vectors.

Vectors that are functional in plants can be binary plasmids derived from *Agrobacterium*. Such vectors are capable of transforming plant cells. These vectors contain left and right border sequences that are required for integration into the host (plant) chromosome. At a minimum, between these border sequences is the gene to be expressed under control of the promoter. In preferred embodiments, a selectable marker and a reporter gene are also included. For ease of obtaining sufficient quantities of vector, a bacterial origin that allows replication in *E. coli* is preferred.

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. (1983) *EMBO J.* 2:987-992; methotrexate, Herrera Estrella et al. (1983) *Nature* 303:209-213; Meijer et al. (1991) *Plant Mol. Biol.* 16:807-820; hygromycin, Waldron et al. (1985) *Plant*

Mol. Biol. 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419-423; glyphosate, Shaw et al. (1986) *Science* 233:478-481; phosphinothricin, DeBlock et al. (1987) *EMBO J.* 6:2513-2518.

Other genes that could serve utility in the recovery of transgenic events but might not be required in the final product would include, but are not limited to, examples such as GUS (β-glucuronidase), Jefferson (1987) *Plant Mol. Biol. Rep.* 5:387); GFP (green fluorescence protein), Chalfie et al. (1994) *Science* 263:802; luciferase, Teeri et al. (1989) *EMBO J.* 8:343; and the maize genes encoding for anthocyanin production, Ludwig et al. (1990) *Science* 247:449.

The transformation vector comprising the particular promoter sequence of the present invention, operably linked to a heterologous nucleotide sequence of interest in an expression cassette, can be used to transform any plant. In this manner, genetically modified plants, plant cells, plant tissue, seed, and the like can be obtained. Transformation protocols can vary depending on the type of plant or plant cell targeted for transformation, i.e., monocot or dicot. Suitable methods of transforming plant cells include microinjection, Crossway et al. (1986) *Biotechniques* 4:320-334; electroporation, Riggs et al. (1986) *Proc. Natl. Acad. Sci. USA* 83:5602-5606; Agrobacterium-mediated transformation, see for example, Townsend et al. U.S. Pat. No. 5,563,055; direct gene transfer, Paszkowski et al. (1984) *EMBO J.* 3:2717-2722; and ballistic particle acceleration, see for example, Sanford et al. U.S. Pat. No. 4,945,050 and Tomes et al., U.S. Pat. No. 6,258,999; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926. Also see Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) *Nature (London)* 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. G. P. Chapman et al. (Longman, New York), pp. 197-209 (pollen); Kaeppler et al. (1990) *Plant Cell Reports* 9:415-418; and Kaeppler et al. (1992) *Theor. Appl. Genet.* 84:560-566 (whisker-mediated transformation); D. Halluin et al. (1992) *Plant Cell* 4:1495-1505 (electroporation); Li et al. (1993) *Plant Cell Reports* 12:250-255 and Christou et al. (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed can be grown into plants in accordance with conventional ways. See, for example, McCormick et al. (1986) *Plant Cell Reports* 5:81-84. These plants can then be grown, and pollinated with the same transformed strain or different strains. The resulting plant or plants having expression of the desired characteristic in preferred tissues and under stress conditions of interest can then be identified. Two or more generations can be grown to ensure that tissue-preferred expression of the desired phenotypic characteristic under conditions of interest is stably maintained and inherited.

One of skill in the art would recognize that in certain embodiments the constructs of the present invention, comprising a promoter which is induced by abiotic stress, can be stacked with any combination of polynucleotide sequences of interest in order to create plants with a desired phenotype. The combinations generated can also include multiple copies of any one or more of the polynucleotides of interest. For example, the polynucleotides of the present invention can be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123); increased digestibility (e.g., modified storage proteins (U.S. application Ser. No. 10/053,410, filed Nov. 7, 2001); and thioredoxins (U.S. application Ser. No. 10/005,429, filed Dec. 3, 2001), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene); and traits desirable for processing or process products such as high oil (e.g., U.S. Pat. No. 6,232,529); modified oils (e.g., fatty acid desaturase genes (U.S. Pat. No. 5,952,544; WO 94/11516); modified starches (e.g., ADPG pyrophosphorylases (AGPase), starch synthases (SS), starch branching enzymes (SBE) and starch debranching enzymes (SDBE); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) which facilitate expression of polyhydroxyalkanoates (PHAs), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method, including but not limited to, cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of a polynucleotide of interest. This may be combined with any combination of other suppression cassettes or overexpression cassettes to generate the desired combination of traits in the plant.

The following examples are offered by way of illustration and not by way of limitation.

EXAMPLES

Example 1

Expression of Zea Mays ARDA-1 Under Stress Conditions

Through gene expression profiling of female reproductive tissue using cDNA microarrays and the Affymetrix Gene Chip® system (Affymetrix, Inc., Santa Clara, Calif.), a gene was identified as being upregulated in female reproductive tissues of Zea mays during abiotic stress. Stress conditions evaluated included acute shade and drought, as well as chronic drought and high density. Under mild drought stress, expression doubled in pedicel tissue and increased by a factor of ten in ear tissue. Under severe drought stress, expression in the pedicel was as much as 17-fold higher than in non-stress conditions. The gene has been named ZmARDA-1 and is orthologous to an auxin-repressed, dormancy-associated gene previously isolated from pea and strawberry. (Stafstrom et al., Planta 205:547-552, 1998; Reddy et al., Plant Mol. Biol. 14:127-136, 1990)

In situ hybridization of a ZmARDA-1 probe to ear tips grown under high plant density confirmed that ZmARDA-1 expression was elevated under stress. Furthermore, the hybridization signal was not uniformly distributed across the ear tip; rather, it was restricted to developing florets of the ear. Closer examination of the in situ hybridization results showed a clear gradient from the apex to the base of the ear tip, with the strongest signal occurring in the uppermost florets. A consistent expression gradient was also apparent within individual spikelets; that is, expression was relatively weak at the base of the spikelet and gradually increased in the direction of the carpel primordia.

In addition, Northern evaluation showed that a dying maize ear tip produces a 10-fold increase in ZmARDA-1 transcripts relative to a healthy tip. Thus, elevated ZmARDA-1 signal may be an indicator of floret abortion.

Example 2

Isolation of ZmARDA-1 Promoter Sequence

The promoter region for the Zea mays ARDA-1 gene was isolated using the GenomeWalker™ kit (Clontech, Palo Alto, Calif.). A sequence for the ZmARDA-1 promoter region is set forth in SEQ ID NO:1.

The procedure for promoter isolation is described in the User Manual for the GenomeWalker™ kit sold by Clontech Laboratories, Inc., Palo Alto, Calif. DNA was isolated from a BAC (bacterial artificial chromosome) clone comprising the ZmARDA gene. Precipitated DNA was recovered using an inoculation loop and transferred to a 1.5 ml eppendorf tube containing 500 µl of TE (10 mM Tris pH 8.0, 1 mM EDTA). The DNA was allowed to dissolve at room temperature for 15 minutes, phenol extracted and 2-propanol precipitated in 700 µl. The precipitate was recovered and washed with 70% ethanol. The DNA was then placed in a clean 1.5 ml eppendorf tube to air dry and resuspended in 200 µl of TE. RNase A was added to 10 µg/ml and the mixture was incubated at 37° C. for several hours. The DNA was then extracted once with phenol-chloroform, then chloroform, then ethanol precipitated and resuspended in TE. The DNA was then used exactly as described in the GenomeWalker™ User Manual (Clontech PT3042-1 version PR68687). Briefly, the DNA was digested separately with restriction enzymes DraI, EcoRV, PvuII, ScaI, and StuI, all blunt-end cutters. The DNA was extracted with phenol, then chloroform, then ethanol precipitated. The GenomeWalker™ adapters were ligated onto the ends of the restricted DNA.

For isolation of the specific promoter region, a gene-specific primer (TGGTGGCCTTGCGGAGCTTCTC; SEQ ID NO: 4) was designed to amplify the region upstream of the coding sequence, i.e. the 5' untranslated region and promoter of the chosen gene. The first round of PCR was performed on each DNA sample with Clontech primer AP1 (SEQ ID NO: 5; 5'-GTAATACGACTCACTATAGGGC-3') and the gene-specific primer.

PCR was performed in a model PTC-100 thermal cycler with HotBonnet™ from MJ Research (Waltham, Mass.) using reagents supplied with the GenomeWalker™ kit. The following cycle parameters were used: 7 cycles of 94° C. for 2 seconds, then 72° C. for 3 minutes, followed by 32 cycles of 94° C. for 2 seconds and 67° C. for 3 minutes. Finally, the samples were held at 67° C. for 4 minutes and then at 4° C. until further analysis.

As described in the User Manual, the DNA from the first round of PCR was then diluted and used as a template in a second round of PCR using the Clontech AP2 primer (SEQ ID NO: 6; 5'-ACTATAGGGCACGCGTGGT-3').

The cycle parameters for the second round were: 5 cycles of 94° C. for 2 seconds, then 72° C. for 3 minutes. Finally, the samples were held at 67° C. for 4 minutes and then held at 4° C. Approximately 10 µl of each reaction were run on a 0.8% agarose gel, and bands (usually 500 bp or larger) were excised, purified with the Sephaglas BandPrep kit (Pharmacia, Piscataway, N.J.) and cloned into the TA vector pCR2.1 (Invitrogen, San Diego, Calif.).

Clones were sequenced for verification. Elements identified within the ZmARDA-1 promoter region include the following:

AuxRR-core (two sites), a cis-acting regulatory element involved in auxin responsiveness.

DPBFCOREDCDC3 (two sites), similar to the core sequence for the binding site of the bZIP transcription factors DPBF-1 and DPBF-2 within the promoter of the embryo-specific, ABA-inducible Dc3 gene from Daucus carota. A bZIP transcription factor in Arabidopsis is encoded by the abscisic acid response gene ABI5.

ABRE, a cis-acting element involved in abscisic acid responsiveness.

MBS, an MYB binding site.

CATATGGMSAUR, an element of the SAUR (Small Auxin-Up RNA) 15A gene promoter in soybean, involved in auxin responsiveness ASF1MOTIFCAMV, a TGACG motif found in many promoters and involved in transcriptional activation of several genes by auxin and/or salicylic acid; may be relevant to light regulation; binding site for ASF-1 in the CaMV 35S promoter, and for the TGA1a binding protein in tobacco.

ARFAT, an auxin-response factor binding site found in the promoters of primary/early auxin-response genes of *Arabidopsis*; binding site of *Arabidopsis* ARF1. The sequence is also found in the NDE element of the *Glycine max* SAUR 15A promoter and in the D1 or D4 element in the *Glycine max* GH3 promoter.

ABADESI2, an element which mediates response to ABA and is related to desiccation; expression is directed to seeds.

CE3, a cis-acting element involved in ABA and VP1 responsiveness.

TATC-box, a cis-acting element involved in gibberellin responsiveness.

CGTCA-motif, a cis-acting element involved in methyl-jasmonate responsiveness.

Example 3

Expression of Transgenes in Monocot Cells

A plasmid vector is constructed comprising the ZmARDA-1 promoter operably linked to a heterologous nucleotide sequence. This construct can then be introduced into maize cells by the following procedure.

Immature maize embryos are dissected from developing caryopses derived from crosses of the inbred maize lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus, consisting of undifferentiated masses of cells with somatic proembryoids and embryoids borne on suspensor structures, proliferates from the scutellum of these immature embryos. The embryogenic callus isolated from the primary explant can be cultured on N6 medium and sub-cultured on is this medium every 2 to 3 weeks.

The plasmid p35S/Ac (Hoechst Ag, Frankfurt, Germany) or equivalent may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73; U.S. Pat. No. 4,945,050) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton flying disc (Bio-Rad Labs). The particles are then accelerated into the corn tissue with a Biolistic PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 4

Expression of Transgenes in Dicot Cells

Soybean embryos are bombarded with a plasmid containing a heterologous sequence operably linked to the ZmARDA-1 promoter as follows. To induce somatic embryos, cotyledons of 3-5 mm in length are dissected from surface-sterilized, immature seeds of the soybean cultivar A2872, then cultured in the light or dark at 26° C. on an appropriate agar medium for six to ten weeks. Somatic embryos producing secondary embryos are then excised and placed into a suitable liquid medium. After repeated selection for clusters of somatic embryos that multiply as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the heterologous sequence operably linked to the ZmARDA-1 promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Identification of the Gene From a Computer Homology Search

Gene identities can be determined, for example, by conducting BLAST (Basic Local Alignment Search Tool; Altschul, S. F., et al., (1993) J. Mol. Biol. 215:403-410) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN program. The DNA sequences are translated in all reading frames and compared for similarity to all publicly available protein sequences contained in the "nr" database using the BLASTX program (Gish, W. and States, D. J. *Nature Genetics* 3:266-272 (1993)) provided by the NCBI. In some cases, the sequencing data from two or more clones containing overlapping segments of DNA are used to construct contiguous DNA sequences.

Sequence alignments and percent identity calculations can be performed using software such as the Megalign program of the LASERGENE bioinformatics computing suite (DNASTAR Inc., Madison, Wis.), or BestFit or GAP in the Genetics Computer Group (GCG®) set of programs, Accelrys, Inc., San Diego, Calif. Default parameters for BestFit include a gap creation penalty of 50 and a gap extension penalty of 3. Multiple alignment of the sequences can be performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

All publications and patent applications cited in the specification are indicative of the level of skill of those in the art to which this invention pertains. All publications, patents, patent applications, and computer programs cited herein are incorporated by reference to the same extent as if specifically and individually indicated to be incorporated by reference.

Although the foregoing invention has been described in some detail by way of illustration and example for purposes of clarity of understanding, it will be apparent to one of ordinary skill in the art that certain changes and modifications can be practiced within the scope of the appended claims.

We claim:

1. An isolated promoter which is induced by abiotic stress and comprises a polynucleotide of SEQ ID NO: 1.

2. An expression cassette comprising the promoter of claim 1 and a polynucleotide operably linked to said promoter, wherein said promoter is capable of initiating transcription of said linked palynucleotide in a plant transformed with said expression cassette.

3. A transformation vector comprising the expression cassette of claim 2.

4. A plant, or its parts, stably transformed with the expression cassette of claim 2.

5. The plant of claim 4 further comprising a second isolated promoter operably linked to a second polynucleotide of interest.

6. The plant of claim 5 wherein transformation is accomplished with a single expression cassette.

7. The plant of claim 5 wherein transformation is accomplished with multiple expression cassettes.

8. The plant parts of claim 4, wherein said parts are selected from the group consisting of: cells, protoplasts, cell tissue cultures, callus, cell clumps, embryos, pollen, ovules, seeds, flowers, kernels, ears, cobs, leaves, husks, stalks, roots, root tips, anthers, and silk.

* * * * *